United States Patent [19]

Coleman et al.

[11] 4,380,650

[45] Apr. 19, 1983

[54] LACTONE PROCESS

[75] Inventors: James P. Coleman; Richard C. Hallcher, both of Maryland Heights; Dudley E. McMackins, St. Charles, all of Mo.

[73] Assignee: Monsanto Company, St.Louis, Mo.

[21] Appl. No.: 222,199

[22] Filed: Jan. 2, 1981

[51] Int. Cl.$^3$ ............................................. C07D 307/32
[52] U.S. Cl. ...................................... 549/326; 562/601
[58] Field of Search ........................ 260/343.6; 549/326

[56] References Cited

U.S. PATENT DOCUMENTS

| | | | |
|---|---|---|---|
| 2,359,096 | 9/1944 | Elderfield | 260/343.6 |
| 3,155,685 | 11/1964 | Prill et al. | 260/343.6 |
| 3,868,370 | 2/1975 | Smith | 260/343.6 |
| 3,927,051 | 12/1975 | de Klein | 260/413 |
| 3,980,670 | 9/1976 | Kummer et al. | 260/343.6 |
| 4,011,239 | 3/1977 | Heiba et al. | 260/327 S |
| 4,014,910 | 3/1977 | de Klein | 260/413 |
| 4,022,822 | 5/1977 | Tsujino et al. | 260/343.6 |
| 4,158,741 | 6/1979 | Goi et al. | 562/600 |
| 4,175,089 | 11/1979 | Heiba et al. | 260/343.6 |

OTHER PUBLICATIONS

Houben–Weyl, Methoden der Organischen Chemie, vol. VI/2 (1963), pp. 579–580.
W. J. de Klein, Journal of the Royal Netherlands Chemical Society, vol. 94/7, (Jul. 1975), pp. 151–153.
W. J. de Klein, Journal of the Royal Netherlands Chemical Society, vol. 94/2, (Feb. 1975), pp. 48–50.
W. J. de Klein, Journal of the Royal Netherlands Chemical Society, vol. 96/1, (Jan. 1977), pp. 22–25.

*Primary Examiner*—Norma S. Milestone
*Attorney, Agent, or Firm*—Joseph D. Kennedy; James W. Williams, Jr.

[57] ABSTRACT

Acyloxyhexenoic acids are converted to $\gamma$-vinyl-$\gamma$-butyrolactone.

22 Claims, No Drawings

LACTONE PROCESS

The present invention relates to the conversion of acyloxyhexenoic acids to γ-vinyl-γ-butyrolactone. The conversion is readily accomplished under hydrolytic conditions or similar conditions.

BACKGROUND OF THE INVENTION

γ-vinyl-γ-butyrolactone is a compound which has been reported to be useful for conversion to sorbic acids; see U.S. Pat. Nos. 4,022,822 and 4,158,741. γ-vinyl-γ-butyrolactone has been reported to be prepared in a reaction of butadiene and acetic acid with trivalent manganese at elevated temperature; see U.S. Pat. No 4,175,089. In a copending application Ser. No. 222,200 filed of even date herewith, applicants have claimed a process for preparing acyloxyhexenoic acids by reaction of butadiene and acetic acid with metal oxidants.

SUMMARY OF THE INVENTION

It has been found that acyloxyhexenoic acids, particularly 4-acetoxy-5-hexenoic acid and 6-acetoxy-4-hexenoic acid, can be readily converted to γ-vinyl-γ-butyrolactone under hydrolytic or other conditions suitable for elimination of acetic acid from the acyloxyhexenoic acid molecule, as by use of acidic or basic catalysts. An acidic ion exchange resin is particularly effective for such conversion. While the γ-vinyl-γ-butyrolactone itself can undergo further reaction to produce sorbic acid, the process can be conducted so that substantial quantities of the lactone are subject to isolation.

DETAILED DISCLOSURE

As indicated above, applicants have a process for preparing acetoxyhexenoic acids as described in the referenced patent application. In addition, applicants have found that such acetoxyacids can be converted to sorbic acid by a process described in another patent application. Ser. No. 222,201, filed of even date herewith. The present process can be considered a step in an alternate route to sorbic acid, as the lactone produced in the present process can be converted to sorbic acid. However, γ-vinyl-γ-butyrolactone is a known compound with other known or potential uses, so the present process will also be useful when the lactone is the desired final product.

The desired transformation of acyloxyacids to γ-vinyl-γ-butyrolactone can be effected under mild conditions. An acid catalyst is capable of effecting the reaction under ambient conditions, but heating is generally employed. The process is carried out by maintaining the acyloxyacids in contact with an acid catalyst for a time sufficient to effect the desired degree of conversion. Temperatures from ambient to 250° C. or so can be used, but with a fairly reactive catalyst there is advantage in employing relatively mild temperatures, such as temperatures not over about 70° C. to avoid production of substantial amounts of sorbic acid. Thus temperatures of about 30° to about 70° C. can conveniently be used. If higher temperatures are employed, good selectivity to the lactone can still be obtained by use of short reaction times, and it may be convenient to operate in the range of about 60° to about 140° C. Of course, the particular catalyst and its concentration also influences the reaction, and some acid catalysts give good selectivity to the lactone even with relatively high temperatures and long reaction times.

Acid catalysts in general can be used in the reaction, as for example, the type of catalysts used for saponification or esterification reactions. Mineral acids or other acids capable of providing hydrogen ions can be used, including various acids classified as Lewis acids. Various mineral acids and acidic ion exchange resins are convenient for use. Various metal oxides can also be employed, particularly acidic metal oxides, e.g. silica aluminas, thorium oxide, etc. Dehydration catalysts can be used, such as various metal oxides known as dehydration catalysts. In general, catalysts useful in other lactone formation reactions are expected to be useful in the present reaction. Among the mineral acids useful or potentially useful are hydrochloric, sulfuric and phosphoric acids, along with other sulfur and phosphorus acids, e.g. aromatic sulfonic acids and aliphatic sulfonic acids, and various salts and acid salts of such acids. The catalysts disclosed in the aforesaid U.S. Pat. No. 4,022,822 and 4,158,741 can be used with some degree of success to convert acetoxyhexenoic acids to γ-vinyl-γ-butyrolactone, although results will vary with different catalysts. Various catalysts which can be used herein include the ion exchange resins, Amberlyst ® 15, Amberlyst XN 1005, Amberlyst XN 1010, Amberlite IR-120B, all strongly acidic cation exchange resins, particularly polystyrenes with acidic groups, e.g. sulfonate groups (-SO$_3$H), and marketed by Rohm and Haas Company under the foregoing trademarks; Nafion ® N-501, a sulfonated fluoroether polymer; and Dowex ® 50WX8 polymer, a styrene divinylbenzene copolymer with acid groups. In general catalysts which supply sufficient hydrogen ion can be used, and the reaction can be viewed as occurring in the presence of hydrogen ions. If water is present, even acids such as acetic acid provide sufficient hydrogen ion and the lactone can be prepared by heating the acetoxyhexenoic acids in aqueous acetic acid. Various bases can also be used to effect the reaction, e.g. KOH or other alkali metal hydroxides in aqueous or other media. Thus the reaction occurs under acidic or basic conditions, which in aqueous media involve the presence of hydrogen or hydroxide ions.

Good conversions and selectivities are obtained with some ion exchange resins. In addition, the ion exchange resins generally have the advantage of not dissolving in the acetoxyacids or the solvents utilized, and can be conveniently separated from the lactone product. The acetoxyacids can be reacted in bulk, but use of solvents may be convenient, particularly if the acetoxyacids as obtained are in acetic acid or other solvent. If solvents are used, inert solvents are generally suitable. Acetic and other alkanoic acids and their esters can conveniently be used, as well as aliphatic and aromatic hydrocarbons, e.g. saturated hydrocarbons such as octane, decane, dodecane, etc., aromatic hydrocarbons, including benzene, toluene etc., and halogenated solvents such as chlorobenzene. Ether and other oxygen containing and polar solvents can be used, including for example, dioxane. If a solvent is used, concentrations of the acetoxyhexenoic acids therein can vary widely, e.g. from less than 1% to over 90% by weight.

Acyloxyhexenoic acids are in general suitable for conversion to lactone. However such acids with acetoxy as the acyloxy group are most conveniently prepared by procedures of copending applications. Acyloxyhexenoic acids where the acyloxy is the residue of other alkanoic acids, e.g. RCH$_2$COO-, where R is an alkyl of 1 to 4 carbon atoms, can be converted to the γ-vinyl-γ-butyrolactone by procedures described herein. However, the reactions of butadiene with propionic or higher acids will result in acyloxyhexenoic acids in which there is an alkyl substituent on the 2-carbon atom of the hexenoic acid, corresponding to the R group of the alkanoic acid. Thus further treatment in accordance with procedures herein for conversion to lactone will produce a substituted lactone, i.e. with an alkyl substituent on the alpha carbon atom, i.e., the carbon atom adjacent to the carbonyl of the lactone. Procedures can be used for preparing unsubstituted acyloxyhexenoic acids, such as using mixtures of acetics and another acid in the reaction with butadiene, and separating the mixture of products if necessary; or by some ester exchange reaction with acetoxyhexenoic acids. In practice there may be no reason to employ any acyloxyhexenoic acids other than the acetoxy, because of convenience in preparation, but the others can be converted in accord with procedures described herein. The 6-acyloxy-4-hexenoic and 4-acyloxy-5-hexenoic are particularly appropriate for use herein, but various isomers are expected to be similarly useful in varying degree. Methods of isomerization are known which will change the position of the double bond and the acyloxy-substituent.

The following examples are illustrative of the invention.

EXAMPLE 1

A mixture of 6-acetoxy-4-hexenoic acid and 4-acetoxy-5-hexenoic acid, 10 grams in 40 grams acetic acid was mixed with Amberlyst ® 15 exchange resin, and quickly heated to 100° C. A sample taken at six minutes showed 74% of the acetoxyacids had been converted to γ-vinyl-γ-butyrolactone and 7% to sorbic acid and its isomers. At 15 minutes, the conversion was 70% to the lactone, and 17.4% to sorbic acid. At 30 minutes the amount of lactone and sorbic product were nearly equivalent.

EXAMPLE 2

The procedure of Example 1 was repeated, but at 120° C. At three minutes there was 70% conversion of the acetoxyhexenoic acids to γ-vinyl-γ-butyrolactone and 10.49% conversion to sorbic acid and its isomers. At 6 minutes, the conversion to lactone was 57%, and 22% to sorbic products. At 9 minutes, the lactone product still exceeds the sorbic product. Even after extended time so that no acetoxyacids remain, there is still a small amount of lactone product.

EXAMPLE 3

A 1 gram amount of acetoxyhexenoic acids in 6 ml hydrochloric acid (37%) was heated for 2 hours at 100° C. to cause 98% conversion with 17% selectivity to sorbic acid and 69% to γ-vinyl-γ-butyrolactone. The sorbic acid may include a small amount of isomeric hexedienoic acids.

EXAMPLE 4

Utilizing amounts of acetoxyacids and Amberlyst ® 15 resin as in previous examples, the components were heated in chlorobenzene solvent at 85° C. for 2.5 hours to give 53% selectivity to sorbic acid and 7% to its isomers, with 12% selectivity to lactone. When a small amount of tetrabutylammonium iodide was also present, the selectivity to sorbic acid was 45%. Cutting the reaction time to 1.5 hours gave 47% selectivity to sorbic acid and 26% to lactone. An additional procedure in which 1.6 grams of the acetoxyacids were heated to 85° C. with 3 grams of the resin in 10 ml of chlorobenzene gave 64% selectivity to sorbic acid and 77% to sorbic plus isomers.

EXAMPLE 5

An 0.8 gram amount of acetoxyhexenoic acids and 1.5 grams particulate silica/alumina, (87/13 SiO$_2$/Al$_2$O$_3$) containing 2% fluorine was heated to 100° C. in 5 ml dioxane for 1.7 hours. The reaction caused 98% conversion with 90% selectivity to γ-vinyl-γ-butyrolactone and 6% to sorbic acids. When 1.5 grams of the silica alumina in 5 grams of the acetoxyacids without solvent was heated to 140° C. for 0.3 hours, there was 87% selectivity to the lactone. Another procedure with a silica/alumina and no solvent at 150° C. for 1 hour gave 55% conversion to the lactone.

EXAMPLE 6

Acetoxyhexenoic acids were heated with Pd(P(C$_6$H$_5$)$_3$)$_4$ and NaBr to 120° C. for 1 hour to give approximately 70% conversion to the lactone. When pyridine was also present, there was approximately 90% conversion in 5 hours.

EXAMPLE 7

Acetoxy acids (6.0 g) were heated at 45° in a mixture of acetic acid (25.0 g) and sulfuric acid (0.35 g) for one hour. Selectivity to lactone was 86% with a mass balance of 100%. No sorbic acid was observed.

EXAMPLE 8

Acetoxy acids (5 g) were heated at 90° in methylene chloride (30 ml) for three hours over 9 g of Amberlyst resin. The reaction was carried out in a pressure bottle at ~50 psi. Selectivity to sorbic was 78% with an 84% mass balance.

EXAMPLE 9

Acetoxy acids (65 g) were heated at reflux (~45° C.) methylene chloride (300 g) over 100 g of Amberlyst resin for 17.5 hours. At the end of the time the resin was filtered and the resin washed with two 50 ml portions of CH$_2$Cl$_2$. The reaction mixture and washings were extracted three times with 50 ml portions of sodium bicarbonate (saturated). The methylene chloride was evaporated and distillation of the residue gave 28 g of vinyl-butyrolactone (66%).

EXAMPLE 10

Acetoxy acids (5.16 g) were refluxed in 25 ml of water containing (1.85 g KOH). After 3 hours vpc showed a 72% yield of lactone. No sorbic acid was observed and on further heating the amount of lactone decreased.

EXAMPLE 11

Acetoxy acids (5.16 g) were refluxed in 25 ml of tetrahydrofuran containing KOH (1.85 g) and 18-C-6 crown ether (0.2 g) for four hours. Vpc analysis showed lactone (66%) and some unidentified products.

The acetoxyacids utilized herein can be prepared by procedures such as those of Example 12.

EXAMPLE 12

A 600 ml. glass-lined pressure reactor equipped with a dip tube, thermocouple and pressure gauge, was modified to contain electrodes. The area of the graphite electrodes exposed to the reaction medium was 31.6 cm$^2$ and the electrode separation was 3.1 cm. A porous polytetrafluoroethylene membrane covered the cathode. The cell was charged with acetic acid, 110 ml., acetic anhydride 110 ml., sodium acetate, 25 grams, manganous acetate tetrahydrate, 12.5 grams, and 27 grams butadiene. Electrolysis and reaction was carried out at 0.5 ampere for 9.4 hours while the temperature was maintained at 95°–97° C. The pressure increased from 56 to 76 psig, and the applied voltage (to maintain constant current) increased from 18.5 to 23.5. The reaction mixture was stirred by continuously pumping head gas through a sparge tube between the electrodes. At the end of the alloted reaction time, the reaction mixture was heated to evaporate volatiles and the residue was partitioned with diethyl ether and water to effect separation of organic products and salts. The ether was evaporated from the ether layer, leaving crude acetoxyhexenoic acids. Determination of acetoxyacids was accomplished by vapor phase chromatographic analysis of a silylated sample of the crude product, using ethyl myristate as standard. Analysis showed 3.4 grams of acetoxyacids for a current efficiency of 22.5% to this product. The acetoxyacids were identified as 6-acetoxy-4-hexenoic acid and 4-acetoxy-5-hexenoic acid by comparison with an analysis of previously identified samples of these acids, obtained in a similar procedure.

Other procedures for preparing acetoxyacids are disclosed in our aforesaid application (C-07-21-1069), the disclosure of which is incorporated herein by reference.

As disclosed herein, many described procedures produce sorbic acids along with the γ-vinyl-γ-butyrolactone. However, the reactions can be conducted under conditions to produce the lactone predominantly and often with much more than 50% selectivity, as by use of particular catalysts, short reaction times or low reaction temperatures. Even very active acidic ion exchange resins will produce predominantly the lactone if used with short reaction times or temperatures not over about 60° or 70° C.

What is claimed is:

1. The process of converting acyloxyhexenoic acids selected from 6-acyloxy-4-hexenoic acid, 4-acyloxy-5-hexenoic acid and mixtures of same, to γ-vinyl-γ-butyrolactone which comprises reacting such acids under conditions suitable for elimination of the acyloxy moiety for a time sufficient to effect such conversion.

2. The process of claim 1 in which the acyloxyhexenoic acids are contacted with an acid catalyst.

3. The process of claim 2 in which the acid catalyst is a cation exchange resin.

4. The process of claim 2 in which the acid catalyst is a mineral acid.

5. The process of claim 2 in which a short reaction time is employed to avoid conversion of the lactone to other products.

6. The process of claim 1 in which the lactone is removed from the reaction zone within a short time of maximum conversion to lactone.

7. The process of claim 1 in which the acyloxyacids are heated to an elevated temperature.

8. The process of claim 7 in which the temperature is not over 70° C.

9. The process of claim 7 in which the temperature is in the range of about 60° to about 140° C.

10. The process of claim 1 in which acetoxyacids are heated in a solvent in contact with an acidic ion exchange resin for a short time.

11. The process of claim 10 in which the time is less than about 15 minutes.

12. The process of claim 10 in which the reaction is stopped after approximately 90% reaction of the acetoxy acids.

13. The process of claim 10 in which the concentration of the acetoxyacids is in the range of about 10% to about 80% by weight.

14. The process of claim 10 in which acetic acid is present as a solvent.

15. The process of claim 10 in which a hydrocarbon solvent is employed.

16. The process of claim 10 in which chlorobenzene is present as solvent.

17. The process of claim 10 in which dioxane solvent is employed.

18. The process of claim 10 in which methylene chloride solvent is employed.

19. The process of claim 1 in which the acetoxyhexenoic acids are contacted with an inorganic base.

20. The process of claim 1 in which the acetoxyacids are contacted with an alkali metal hydroxide.

21. The process of claim 1 in which a metal oxide such as alumina is employed.

22. The process of claim 1 in which a mixture of 6-acetoxy-4-hexenoic acid and 4-acetoxy-5-hexenoic acid are reacted.

* * * * *